(12) United States Patent
Nelson et al.

(10) Patent No.: US 9,265,533 B2
(45) Date of Patent: Feb. 23, 2016

(54) ROD PERSUADER, SYSTEM AND METHOD

(71) Applicant: AESCULAP IMPLANT SYSTEMS, LLC, Center Valley, PA (US)

(72) Inventors: Gregory Nelson, Center Valley, PA (US); Dennis B Van Blargan, Center Valley, PA (US); James D Hughett, Center Valley, PA (US)

(73) Assignee: AESCULAP IMPLANT SYSTEMS, LLC, Center Valley, PA (US)

( * ) Notice: Subject to any disclaimer, the term of this patent is extended or adjusted under 35 U.S.C. 154(b) by 156 days.

(21) Appl. No.: 14/018,235

(22) Filed: Sep. 4, 2013

(65) Prior Publication Data
US 2015/0066089 A1    Mar. 5, 2015

(51) Int. Cl.
*A61B 17/88* (2006.01)
*A61B 17/70* (2006.01)

(52) U.S. Cl.
CPC ......... *A61B 17/7083* (2013.01); *A61B 17/7002* (2013.01); *A61B 17/7085* (2013.01); *A61B 17/7086* (2013.01); *A61B 17/7091* (2013.01); *Y10T 29/49826* (2015.01)

(58) Field of Classification Search
CPC .................. A61B 17/7083; A61B 17/7002
USPC .................. 606/246, 265, 279, 99, 86 A, 914
See application file for complete search history.

(56) References Cited

U.S. PATENT DOCUMENTS

| | | | |
|---|---|---|---|
| 5,020,519 A | 6/1991 | Hayes et al. | |
| 5,720,751 A | 2/1998 | Jackson | |
| 5,782,830 A | 7/1998 | Farris | |
| 6,183,472 B1 | 2/2001 | Lutz | |
| 6,440,133 B1 | 8/2002 | Beale et al. | |
| 6,511,484 B2 | 1/2003 | Torode et al. | |
| 6,660,006 B2 | 12/2003 | Markworth et al. | |
| 6,790,209 B2 | 9/2004 | Beale et al. | |
| 7,160,300 B2 | 1/2007 | Jackson | |
| 7,278,995 B2 | 10/2007 | Nichols et al. | |

(Continued)

FOREIGN PATENT DOCUMENTS

| | | |
|---|---|---|
| EP | 1 585 436 B1 | 1/2004 |
| EP | 1 574 175 A1 | 9/2005 |

(Continued)

OTHER PUBLICATIONS

The International Search Report for PCT/US14/53925 dated Mar. 31, 2015.

*Primary Examiner* — Pedro Philogene
*Assistant Examiner* — David C Comstock
(74) *Attorney, Agent, or Firm* — Kenealy Vaidya LLP

(57) ABSTRACT

A spinal rod persuader, system and method can include an outer tube, an inner tube, and a locking element. A first actuation mechanism can be movable in a linear fashion along a longitudinal axis direction to cause the locking element to move in a linear fashion over the inner tube and to lock the inner tube onto a pedicle screw. A second actuation mechanism can be rotated to cause the outer tube to move in a longitudinal axis direction with respect to the inner tube to push the spinal rod into a final position with respect to the pedicle screw while the pedicle screw is locked to the inner tube. A slot and/or tab structure can be provided in the outer tube such that actuation of the slot/tab will allow disassembly of the inner tube, outer tube and locking element with respect to each other.

30 Claims, 6 Drawing Sheets

(56) References Cited

U.S. PATENT DOCUMENTS

| | | |
|---|---|---|
| 7,462,182 B2 | 12/2008 | Lim |
| 7,491,207 B2 | 2/2009 | Keyer et al. |
| 7,572,281 B2 | 8/2009 | Runco et al. |
| 7,608,081 B2 | 10/2009 | Abdelgany |
| 7,611,517 B2 | 11/2009 | Lim |
| 7,621,918 B2 | 11/2009 | Jackson |
| 7,625,376 B2 | 12/2009 | Brumfield et al. |
| 7,651,502 B2 | 1/2010 | Jackson |
| 7,722,617 B2 | 5/2010 | Young et al. |
| 7,771,430 B2 | 8/2010 | Jones et al. |
| 7,824,411 B2 | 11/2010 | Varieur et al. |
| 7,824,413 B2 | 11/2010 | Varieur et al. |
| 7,842,044 B2 | 11/2010 | Runco et al. |
| 7,887,539 B2 | 2/2011 | Dunbar, Jr. et al. |
| 7,887,541 B2 | 2/2011 | Runco et al. |
| 7,909,835 B2 | 3/2011 | Oribe et al. |
| 7,985,242 B2 | 7/2011 | Forton et al. |
| 7,988,698 B2 | 8/2011 | Rosenberg et al. |
| 8,096,996 B2 | 1/2012 | Gutierrez et al. |
| 8,123,757 B2 | 2/2012 | Zalenski et al. |
| 8,142,437 B2 | 3/2012 | McLean et al. |
| 8,172,847 B2 | 5/2012 | Dziedzic et al. |
| 8,192,438 B2 | 6/2012 | Garamszegi |
| 8,235,997 B2 | 8/2012 | Hoffman et al. |
| 8,303,595 B2 | 11/2012 | Jones |
| 8,591,515 B2 | 11/2013 | Jackson |
| 8,845,649 B2 | 9/2014 | Jackson |
| 2004/0001819 A1 | 1/2004 | Bolen et al. |
| 2005/0028703 A1 | 2/2005 | Oh |
| 2005/0228392 A1 | 10/2005 | Keyer et al. |
| 2006/0019362 A1 | 1/2006 | Yu et al. |
| 2006/0034498 A1 | 2/2006 | Chang et al. |
| 2006/0036260 A1 | 2/2006 | Runco et al. |
| 2007/0093849 A1 | 4/2007 | Jones et al. |
| 2007/0282337 A1 | 12/2007 | Garamszegi |
| 2008/0103500 A1 | 5/2008 | Chao et al. |
| 2008/0154277 A1 | 6/2008 | Machalk et al. |
| 2008/0234678 A1 | 9/2008 | Gutierrez et al. |
| 2009/0105712 A1 * | 4/2009 | Dauster et al. ............... 606/99 |
| 2009/0112220 A1 | 4/2009 | Kraus |
| 2011/0257692 A1 | 10/2011 | Sandstrom et al. |
| 2011/0313460 A1 * | 12/2011 | McLean et al. ............. 606/264 |
| 2012/0053643 A1 | 3/2012 | Harper |
| 2012/0253402 A1 * | 10/2012 | McLean ..................... 606/264 |

FOREIGN PATENT DOCUMENTS

| | | |
|---|---|---|
| EP | 2 460 483 A1 | 6/2012 |
| FR | 2 863 861 A1 | 6/2005 |
| WO | 03/088856 A1 | 10/2003 |
| WO | 2004/066815 A2 | 8/2004 |
| WO | 2004/069034 A2 | 8/2004 |
| WO | 2005/099602 A2 | 10/2005 |
| WO | 2006/019641 A2 | 2/2006 |
| WO | 2006/020443 A1 | 2/2006 |
| WO | 2006/036324 A2 | 4/2006 |
| WO | 2006/127425 A2 | 11/2006 |
| WO | 2007/040888 A2 | 4/2007 |
| WO | 2007/121061 A2 | 10/2007 |
| WO | 2009/014856 A2 | 1/2009 |
| WO | 2009/152308 A1 | 12/2009 |
| WO | 2010/014296 A1 | 2/2010 |

* cited by examiner

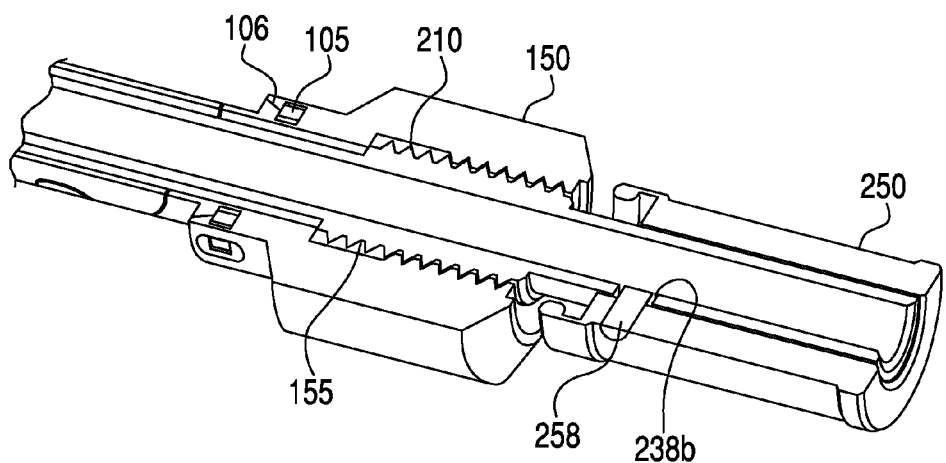
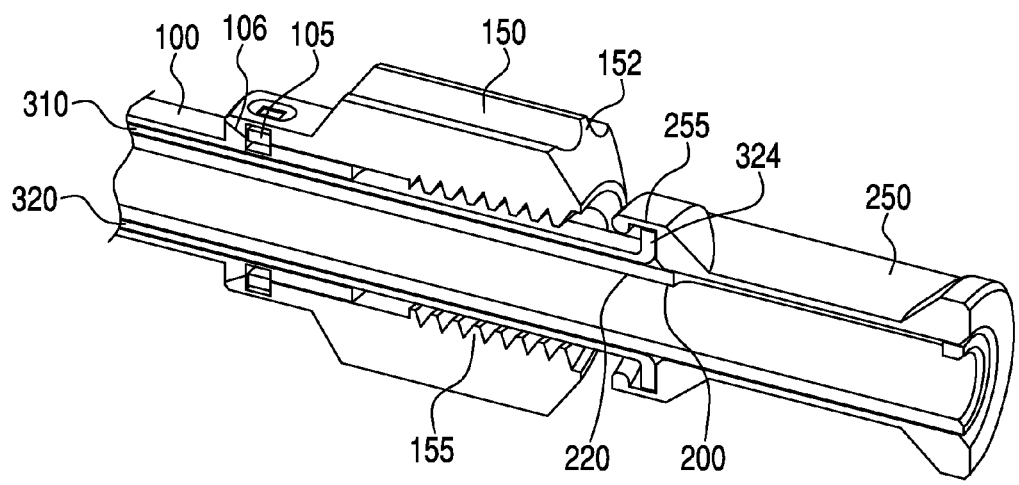

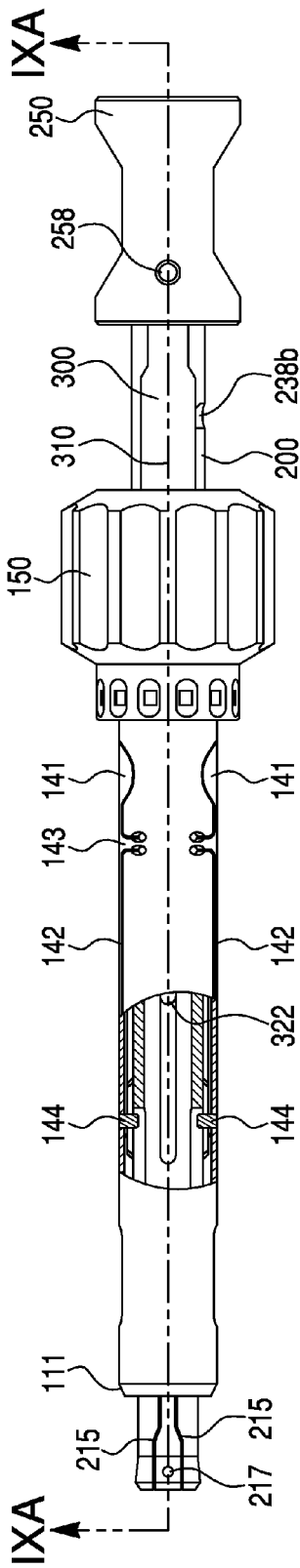
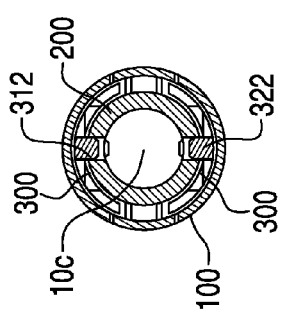
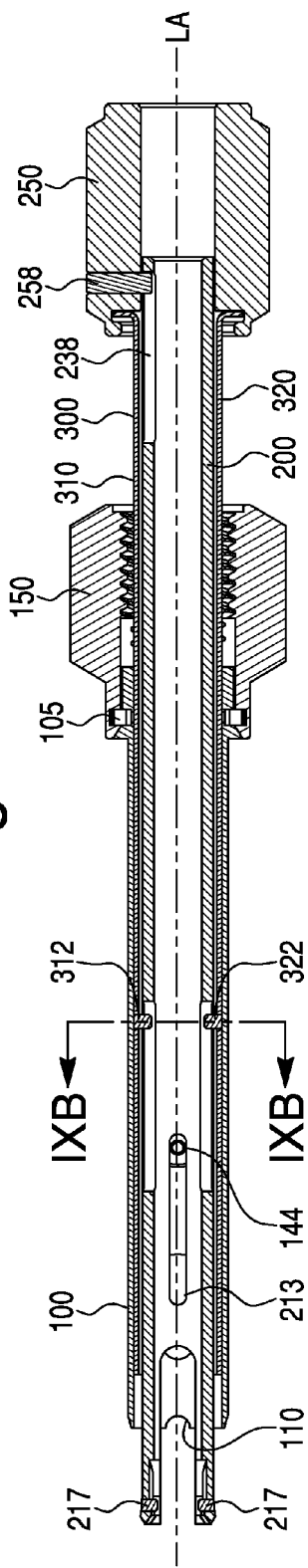

ROD PERSUADER, SYSTEM AND METHOD

BACKGROUND

1. Field

The presently disclosed subject matter relates generally to surgical instrumentation devices, systems, and related methods, and more specifically to a spinal rod persuader device, system and method for use in placing, rearranging, and/or implanting a spinal rod adjacent to vertebrae of a spinal column.

2. Description of the Related Art

In order to stabilize the vertebrae of the spine, medical professionals have typically attached a stabilization rod along the spinal column using a series of pedicle screws attached to vertebrae. Each of the pedicle screws has a threaded portion and a head portion, with the threaded portion including screw threads that can grip each separate vertebrae. The head of the pedicle screw can include a saddle or U-shaped opening into which the spinal rod can be located. Also, set screws can be used to lock the spinal rod into the saddle or U-shaped portion of each of the pedicle screws.

During implantation or other manipulation of the spinal rod and system, a rod persuader is commonly used to persuade the spinal rod into position in the opening in the head of each pedicle screw. In general, alignment of the rod into each of the series of pedicle screws can be difficult to accomplish due to space requirements, variation in alignment of the pedicle screws, and the amount of force required to manipulate and/or bend the spinal rod. Thus, once a spinal rod is in the vicinity of a pedicle screw, a rod persuader has generally been used to simultaneously attach to both the pedicle screw and the spinal rod to urge the spinal rod into a final position within the head of the pedicle screw.

In one known device, the persuader is configured as a trigger operated device in which a distal end of a tube of the persuader is secured to the pedicle screw by a hook or claw that is simply engaged underneath the head or tulip portion of the pedicle screw. Once secured, a push rod is moved downward through the tube by action of a trigger mechanism. The push rod then engages the spinal rod to seat the spinal rod in the pedicle screw. In other devices, both the securing operation and the pushing operation of the persuader can be accomplished by a trigger mechanism. In particular, pulling the trigger a first distance causes gripper portions to engage a side of a pedicle screw. Further motion of the trigger then causes a push rod to engage the spinal rod to seat the spinal rod in the pedicle screw. Finally, another conventional rod persuader device includes first and second screw structures that are operated to both engage a pedicle screw and then to push a spinal rod into place. The conventional rod persuader device typically includes three concentric tubes that all move relative to each other by operation of screw thread mechanisms.

SUMMARY

Accordingly, it may be beneficial to provide a spinal rod persuader device, system, and method that requires minimal space, is easily and accurately operated, and is also easily dismantled for cleaning, inspection, etc. In addition, a need has been uncovered for a device that uses a fundamentally different operating strategy for each of the different operational functions. Moreover, if a screw operation is used to move the push rod, then a different operational strategy, such as linear movement operation, can be used to engage and lock onto the pedicle screw such that the fundamental motion used to cause operation for each of these functions is different and thus can be easily understood and distinguished by a user.

The rod persuader can be used in surgery, for example, during placement of implants for posterior fusion of the spine. In particular the rod persuader can be used by the surgeon (or other technician) to push an ascending rod into the rod receptacle head (tulip) part of the screw implant to which it attaches. The rod persuader accomplishes this by grasping the head of the screw and affixing to it by docking on to features in the polyaxial screw head, for example, S4C which has two holes on the side of the polyaxial screw head body. At the same time the rod persuader can be used to push down on the spinal rod to make it go into the rod receptacle in the screw head.

In addition, the rod persuader maintains the position of the rod in the screw head while the user places a locking screw through a hole in the center of the rod persuader to lock the rod in the head of the screw, and at the same time the polyaxial head.

According to an aspect of the disclosed subject matter, the rod persuader can be helpful when fitting ascending rods to polyaxial screws in the spine, especially when the rod is difficult to place in the screw head. The difficulty of placing the rod in the screw head is quite common for long fusion cases where multiple polyaxial screws are joined in a row or series by one rod and especially when the screws are at slightly different heights relative to the bone in which they are inserted. The surgeon will try to bend the rod to enable the rod to lie in the adjoining screw heads. Such a process can be simplified using a template. Often, however, it is difficult to bend the rod so the rod sits down fully in the polyaxial screw head. In such cases, the rod persuader instrument proves vital.

The cylindrical shape of the rod persuader instrument enables the rod persuader to be used without making a larger incision than is necessary to insert the set screw. The inventive rod persuader of the instant application can therefore be used during less invasive operations which have been shown to reduce patient trauma. The rod persuader is designed for ease of use. In particular, there are two knobs on the proximal end of the instrument. One knob is used to lock the instrument on the polyaxial screw head, by pushing the knob to lock the instrument in position and pulling the knob back to unlock the instrument (i.e. push/pull: lock/unlock). The other knob is rotated to drive the rod down into the rod receptacle of the pedicle screw head (i.e. rotate clockwise to persuade rod/rotate anti-clockwise to let rod go back to its relaxed position). This ease of use is designed into the instrument by having two pushing elements (i.e., lock plates) that run in slots down each side of the long axis of the instrument.

The instrument is designed to be cleanable by dismantling the various components after use. To dismantle, a tab (or tabs) can be pressed in on the side of the rod persuader to release a catch, thus enabling the components of the rod persuader to be removed from each other.

According to one aspect, twin pushing/rotating pieces enable a simpler use (less risk that the user confuses the two knobs on the proximal end of the instrument as one is a push action and the other is rotated). Another aspect is the use of a bendable tab that enables instrument dismantling. Yet another aspect of the presently disclosed subject matter includes slots or flats in the threaded portion of the inner tube into which the pushing pieces (lock plates) slide, along with the simple construction of the lock plates that allows for easy dismantling from the inner tube. An additional aspect of the disclosed subject matter includes an L-shaped slot in the inner tube that provides a track for a pin in the top knob to prevent the knob, when assembled with lock plates, from dropping in the vertical position. Furthermore, when in a locked position, the top knob needs to be rotated before it can be pushed/pulled.

According to one aspect of the disclosure, a spinal rod persuader can include an outer tube including an outer tube distal end and an outer tube proximal end, the outer tube having a central axis coaxial with and extending along a longitudinal axis of the rod persuader. An inner tube can include an inner tube distal end and an inner tube proximal end, the inner tube at least partially located in the outer tube. A locking element can be located between the inner tube and the outer tube, the locking element configured to move with respect to the inner tube from a first unlocked position to a second locked position along a longitudinal axis direction of the inner tube. A second actuation mechanism can be connected to the outer tube such that rotation of the second actuation mechanism with respect to the outer tube causes the outer tube to move in the longitudinal axis direction with respect to the inner tube. A first actuation mechanism can be connected to the locking element such that linear movement of the first actuation mechanism in the longitudinal axis direction causes the locking element to move relative to at least one of the inner tube and outer tube in the longitudinal axis direction. It should be understood that the locking element can comprise a single structure or multiple structures, and can take on various overall shapes, such as a sleeve shape, collar shape, rod(s) shape, etc.

According to another aspect of the disclosed subject matter, a method of using a spinal rod persuader can include providing an outer tube including an outer tube distal end and an outer tube proximal end, the outer tube defining a longitudinal axis of the road persuader, an inner tube including an inner tube distal end and an inner tube proximal end, the inner tube at least partially located in the outer tube, a locking element located between the inner tube and the outer tube, a first actuation mechanism located at a first position along the longitudinal axis of the rod persuader, and a second actuation mechanism located at a second position along the longitudinal axis of the rod persuader. The method can include moving the first actuation mechanism in a linear motion along the longitudinal axis of the rod persuader to cause the locking element to move along the longitudinal axis of the rod persuader. The method can further include rotating the second actuation mechanism relative to the outer tube to cause the outer tube to move along the longitudinal axis of the rod persuader.

In accordance with yet another aspect of the disclosed subject matter, a spinal rod persuader can include an outer tube including an outer tube distal end and an outer tube proximal end, an inner tube including an inner tube distal end and an inner tube proximal end, the inner tube at least partially located in the outer tube, and a locking element located between the inner tube and the outer tube, the locking element including a guide structure configured to guide movement of the locking element with respect to at least one of the outer tube and the inner tube. The outer tube can include a first lock structure located at a first longitudinal axis position of the outer tube and adjacent the guide structure of the locking element, the first lock structure moveable between a locked position and an unlocked position, wherein when the first lock structure is located in the unlocked position, the guide structure of the locking element is permitted to be disassembled from the outer tube and the inner tube, and when the first lock structure is located in the locked position, the guide structure of the locking element is not permitted to be disassembled from the outer tube and the inner tube. The first lock structure can include a first slot having a first portion running along a longitudinal axis of the outer tube, a turn portion located at an end of the first portion, and a second portion running along the longitudinal axis of the outer tube. The first slot can define a first tab and the second slot can define a second tab, and the first tab can be configured such that when a force is applied to the first tab in a direction towards a central longitudinal axis of the outer tube, the first tab moves towards the central longitudinal axis of the outer tube while the second tab simultaneously moves away from the central longitudinal axis of the outer tube.

According to another aspect of the disclosed subject matter, a spinal rod system can include a spinal rod persuader device along with a pedicle screw having a threaded portion and a saddle shaped head portion configured to be engaged by the inner tube of the spinal rod persuader. The system can also include a spinal rod configured to be located within the saddle shaped head portion of the pedicle screw. A device driver can also be included with the system.

BRIEF DESCRIPTION OF THE DRAWINGS

The disclosed subject matter of the present application will now be described in more detail with reference to exemplary embodiments of the apparatus, system and method, given by way of example, and with reference to the accompanying drawings, in which:

FIG. 6 is a perspective cross-sectional partial view taken along line VI-VI of FIG. 2.

FIG. 7 is a perspective cross-sectional partial view taken along line VII-VII of FIG. 2.

FIG. 8 is a front view with partial cutaway of the rod persuader of FIG. 1.

FIG. 9A is a cross-sectional view taken along line IXA-IXA of FIG. 8.

FIG. 9B is a cross-sectional view taken along line IXB-IXB of FIG. 9.

DETAILED DESCRIPTION OF EXEMPLARY EMBODIMENTS

Figure 1:
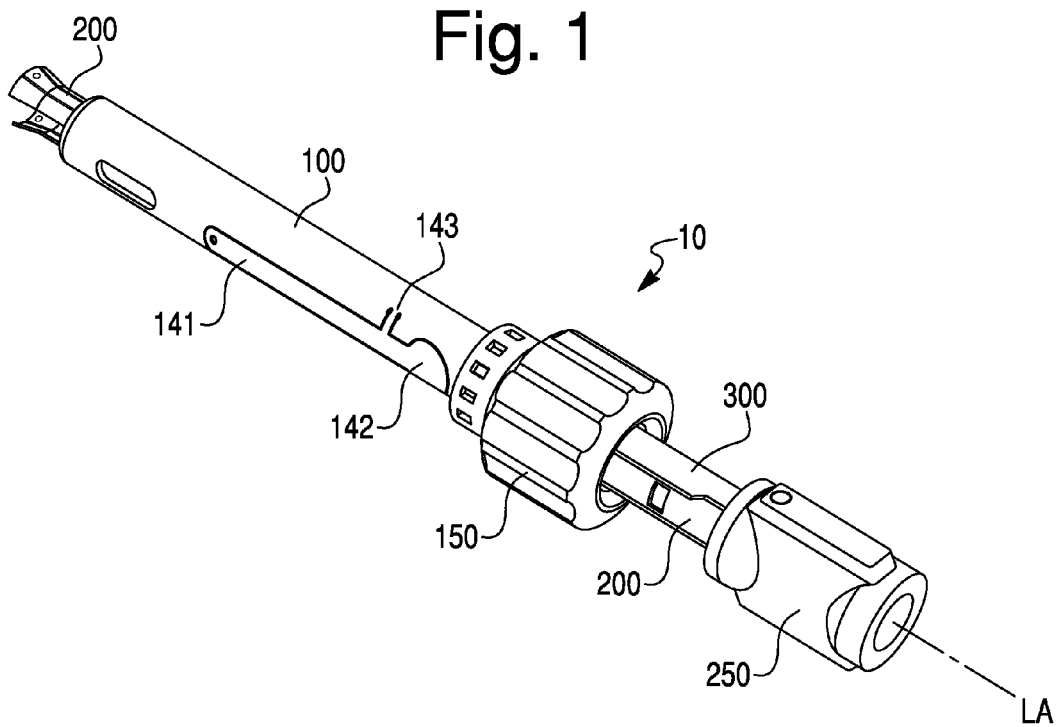
FIG. 1 is a perspective view of an example of a rod persuader device made in accordance with principles of the disclosed subject matter.
Figure 2:
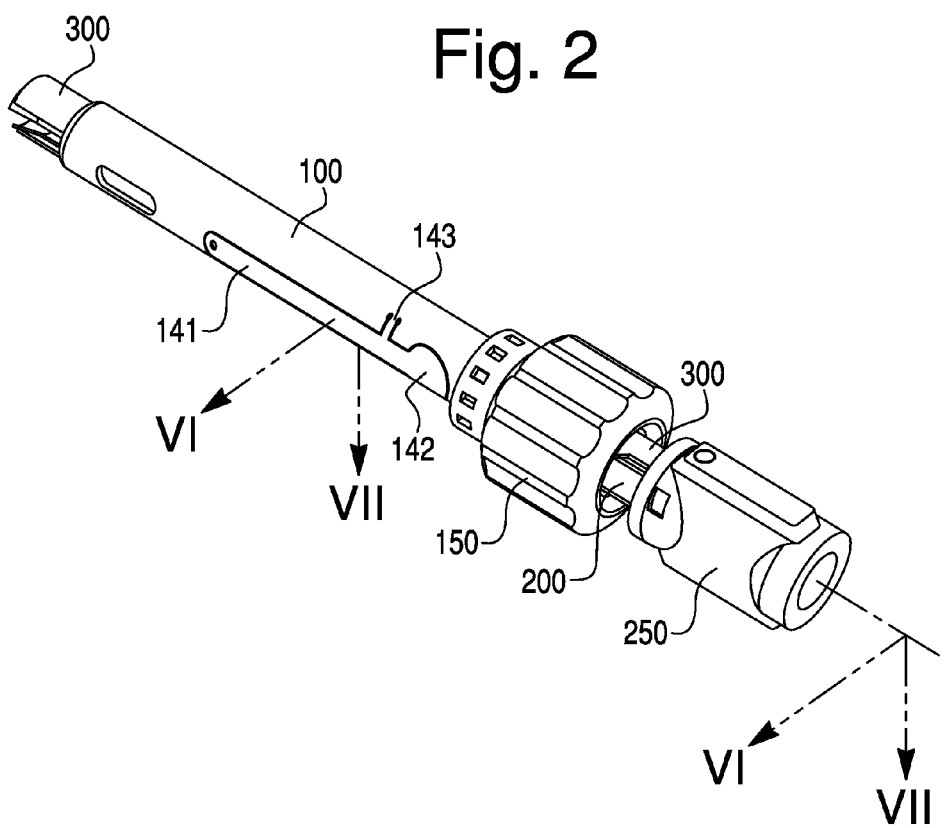
FIG. 2 is a perspective view of the rod persuader of FIG. 1 in a locked configuration.
Figure 10:
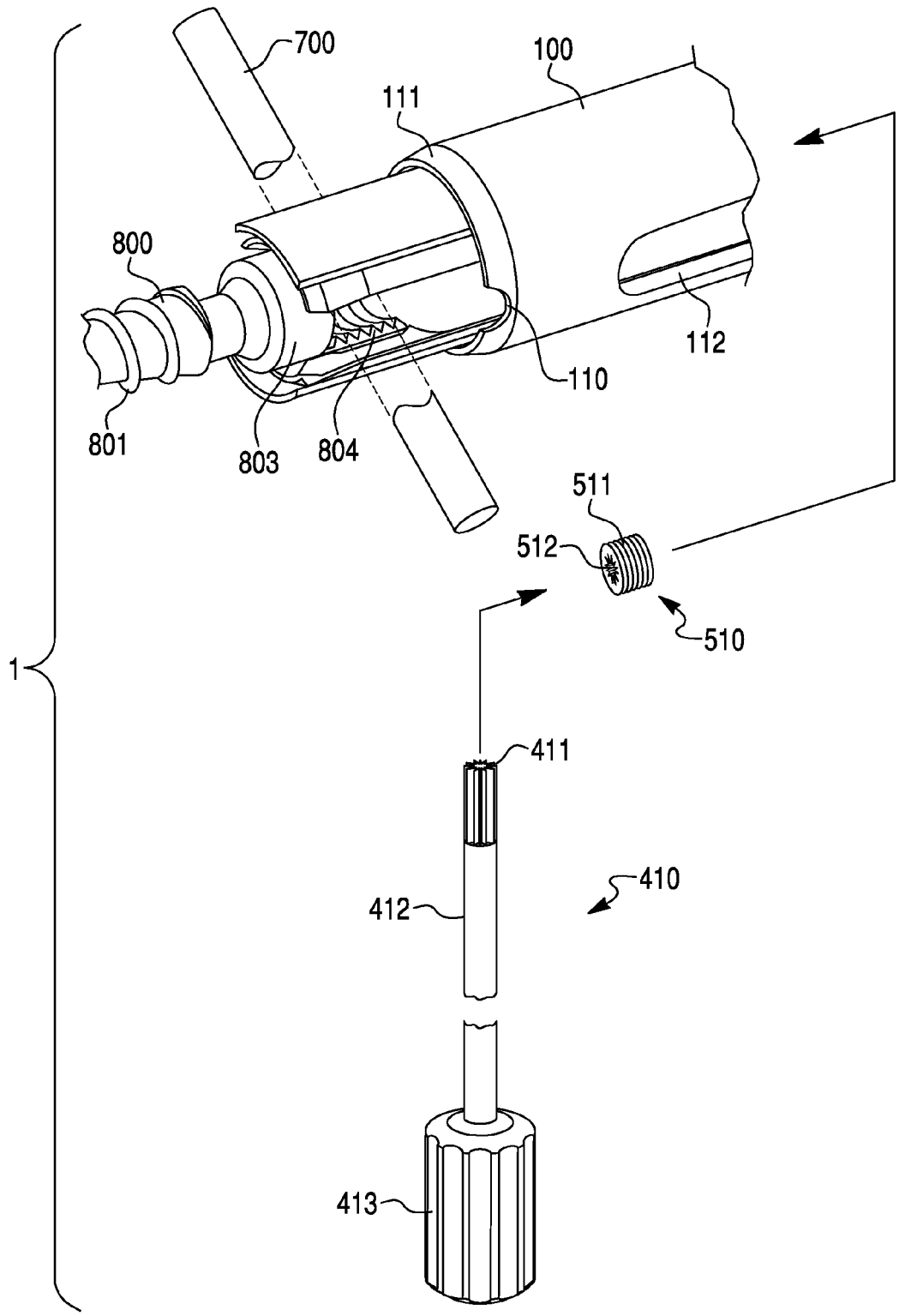
FIG. 10 is a perspective view of an example of a rod persuader system made in accordance with principles of the presently disclosed subject matter.

FIG. 1 is a perspective view of one exemplary embodiment of a rod persuader 10 made in accordance with principles of the disclosed subject matter. The rod persuader 10 can include an outer tube 100, an inner tube 200, and a locking element 300. The distal end of the inner tube 200 can be configured to be attached to a pedicle 800 (FIG. 10) screw during use, while the outer tube 100 can be configured to move relative to the inner tube 200 such that the outer tube 100 contacts and ultimately persuades a spinal rod located adjacent the head of the pedicle screw 800 into a final position seated within the pedicle screw 800. FIG. 1 shows the rod persuader 10 in an unlocked state while FIG. 2 shows the rod persuader 10 in a locked state in which a first actuating mechanism 250 located at a proximal end of the locking element 300 has been moved in a linear fashion to cause a distal end of the locking element 300 to engage a distal end of the inner tube 200 to lock the distal end of the inner tube 200 to a pedicle screw 800 (FIG. 10). Once the inner tube 200 is locked to the pedicle screw 800, a second actuating mechanism 150 can be rotated relative to the outer tube 100 to cause the outer tube 100 to move in a linear fashion towards the distal end of the inner tube 200 (and pedicle screw and spinal rod). A distal tab 141 and a proximal tab 142 can be integrally formed with the outer tube 100 and separated by a living hinge 143 such that force applied to the proximal tab 142 in a direction substantially perpendicular (i.e., perpendicular or almost perpendicular) to a longitudinal axis of the rod persuader 10 causes the distal tab 143 to move away from the longitudinal axis of the rod persuader 10 in a see-saw type action. Actuation of the tabs 141 and 142 about the living hinge 143 allows a user to easily disassemble the outer tube 100 from the inner tube 200 and locking element 300 for cleaning, repair and/or manipulation of different parts for re-assembly.

Figure 3:
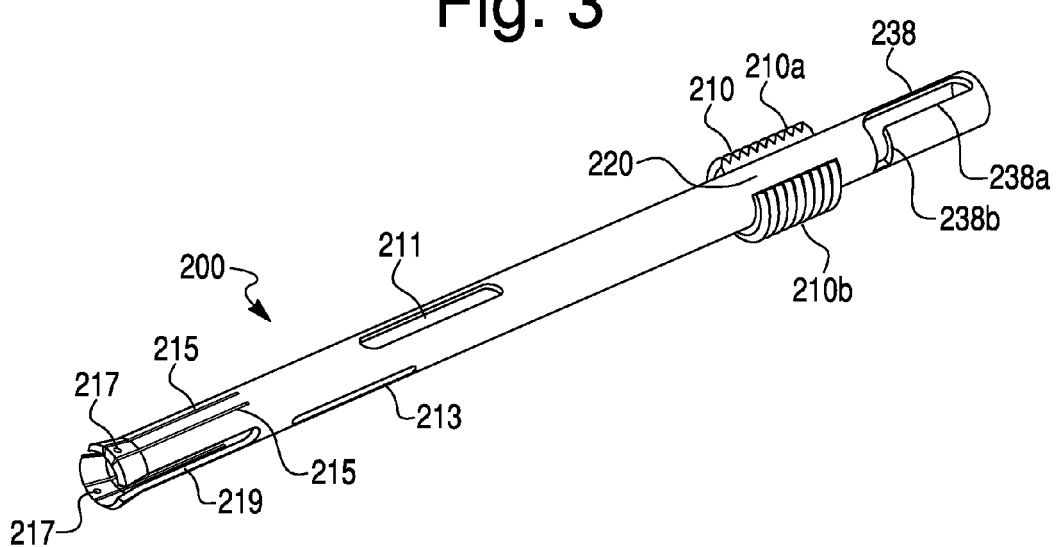
FIG. 3 is a perspective view of the inner tube of the rod persuader of FIG. 1.

FIG. 3 is a perspective view of the inner tube 200 of the rod persuader 10. As indicated above, the inner tube 200 functions to grip a pedicle screw 800 at its distal end while also providing structure that allows for relative motion of the other functioning structures (e.g., the outer tube 100 and locking element 300) of the rod persuader 10. The inner tube 200 can include an external screw thread 210 that includes a first screw thread portion 210a and a second screw thread portion 210b separated by a flat 220 located on either side of the screw thread portion 210a and screw thread portion 210b. Thus, the screw thread 210 is broken into two separate semicircular screw thread portions, 210a and 210b. The design facilitates two lock plates 310 and 320 of the locking element 300 extending along the inner tube 200 in the flat 220 located on each side of the two separate semicircular screw thread portions, 210a and 210b.

A distal end of the inner tube 210 can include a slot 238 for guiding a first actuation mechanism 250. In particular, the slot 238 can be configured in an L-shaped pattern that includes a first linear portion 238a that extends downward in a linear fashion substantially parallel with a longitudinal axis of the inner tube 210. The slot 238 can terminate at its proximal end at a perpendicular portion 238b of the L-shaped slot 238, with the perpendicular portion 238b extending in a direction substantially perpendicular to the longitudinal axis of the inner tube 200. Accordingly, during use, a pin 258 located on the first actuation mechanism 250 can be guided in the L-shaped slot 238 in a first linear direction along the longitudinal axis of the inner tube 200 until reaching a distal and final position in the linear longitudinal slot portion 238b. Once reaching the distal and final position, the first actuation mechanism 250 can be turned or rotated to cause the pin 258 to slidably engage the perpendicular portion 238b of the L-shaped slot 238. Thus, the engagement of the pin 258 with the perpendicular portion 238b of the L-shaped slot 238 can lock the first actuation mechanism 250 (and the lock plates 310 and 320 attached thereto) at a specific location along the longitudinal axis LA of the rod persuader 10.

The inner tube 200 can include two locking element slots 211 that are opposed to each other and located distally of the screw thread 238. A pin 312 and 322 located in each of the locking element plates 310 and 320, respectively, can be located in each of the two locking element slots 211 such that the lock plates 310, 320 are guided in a linear longitudinal axis motion when actuated by the first actuation mechanism 250.

In addition, a pair of opposed outer tube slots 213 can be located distally of the locking element slots 211 in the inner tube 200. Pins 144 located on either side of the outer tube 100 can be located in each of the two outer tube slots 213 in the inner tube 200 such that the outer tube 100 can be guided to move only in a linear longitudinal axis motion when actuated by the second actuator mechanism 150.

The inner tube 200 can include structure at a distal end thereof for attaching and locking to a pedicle screw 800 during use. For example, the distal end of the inner tube 200 can include first and second opposed arms that are separated and defined by opposed openings 219 that run along either side of the inner tube 200. Each of the opposed openings 219 can have a longitudinal axis substantially parallel with the longitudinal axis LA of the rod persuader device 10. In addition, a plurality of distal slots 215 can be formed in each of the opposed arms to form relatively resilient and flexible tabs that include a pin 217 therein for connection and locking to a mating indent or opening in a pedicle screw 800. The opposed arms and opposed flexible tabs can be beveled outward in a trumpet like fashion in order to facilitate quick and easy attachment to the head 802 of the pedicle screw 800 (see, for example, FIG. 10). In addition, the flexible and resilient nature provided by the distal slots 215 allows for the pins 217 to be "snap-fit" onto the head 802 of the pedicle screw 800. As will be described below, the pins 217 and the distal end of the inner tube 200 can be locked onto the head 802 of the pedicle screw 800 by use of a locking element 300 that can be caused to ride over and on top of the beveled distal portion of the inner tube 200 to prevent outward flexation of the arms and tabs, thereby maintaining contact between the pins 217 with mating structures, such as indents, of the pedicle screw 800.

Figure 4:
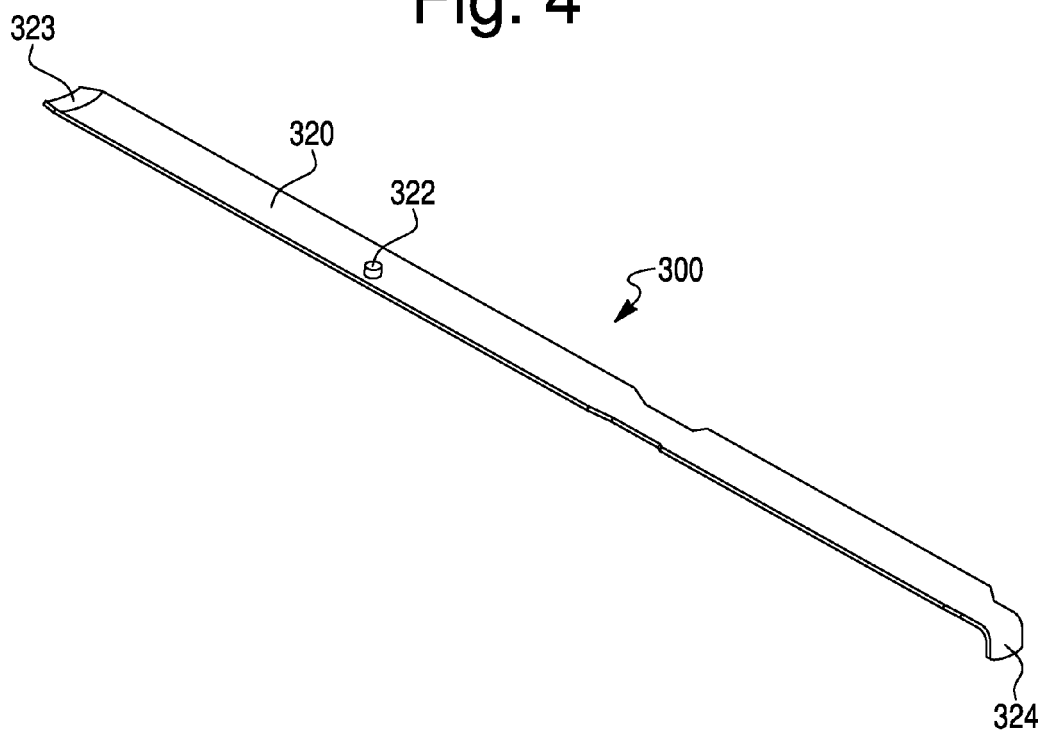
FIG. 4 is a perspective view of the locking element of the rod persuader of FIG. 1.

FIG. 4 shows a perspective view of one lock plate 320 of the locking element 300. It should be understood that another lock plate 310 that is symmetrical to the lock plate 320 can be included to comprise the locking element 300. The lock plates 310 and 320 are on opposite sides of the inner tube 200 with a gap defined between each longitudinally extending and opposing free ends of the lock plates 310 and 320, wherein the lock plates 310 and 320 are disposed intermediate the inner tube 200 and outer tube 100 in a direction extending radially away from a longitudinal axis LA of the rod persuader 10. The lock plate 320 can include a pin 322 configured to be guided within locking element slot 211 in the inner tube 200 to ensure linear movement of the locking element in the longitudinal axis direction of the rod persuader 10. A tab 324 can be located at a proximal end of the lock plate 320 for attachment to the first actuation mechanism 250. The tab 324 can be configured such that it can slide within a slot or channel 255 of the first actuation mechanism 250 to allow the first actuation mechanism 250 to rotate with respect to both the lock plate 320 and the inner tube 200. In addition, the tab 324 can be configured such that movement of the first actuation mechanism 250 in a linear direction substantially parallel with the longitudinal axis LA of the rod persuader 10 will cause the lock plate 320 to also move in a substantially linear fashion substantially parallel with the longitudinal axis LA of the rod persuader 10. Moreover, the pin 322 located in the slot 211 of the inner tube 200 will ensure that only linear motion occurs, and will prevent the lock plate 320 from rotating with the first actuation mechanism 250 when the first actuation mechanism 250 is turned to lock the locking element 300 in place in a linear longitudinal axis position with respect to the inner tube 200. The most distal end 323 of the lock plate 320 can be beveled in order to efficiently mate with the outwardly beveled arms and tabs of the most distal end of inner tube 200. Thus, the most distal end 323 will contact the arms and tabs of the most distal end of inner tube 200 and, because the outer tube 100 constrains outward movement of the locking element 300, the most distal end 323 of the locking element 300 will effectively lock the pin 217 into engagement with a mating structure, such as an indent, in the pedicle screw 800. In this orientation, the rod persuader 10 will be locked to the pedicle screw 800 (see, for example, FIG. 10) and the operation of persuading a spinal rod 700 into place can begin.

Figure 5:
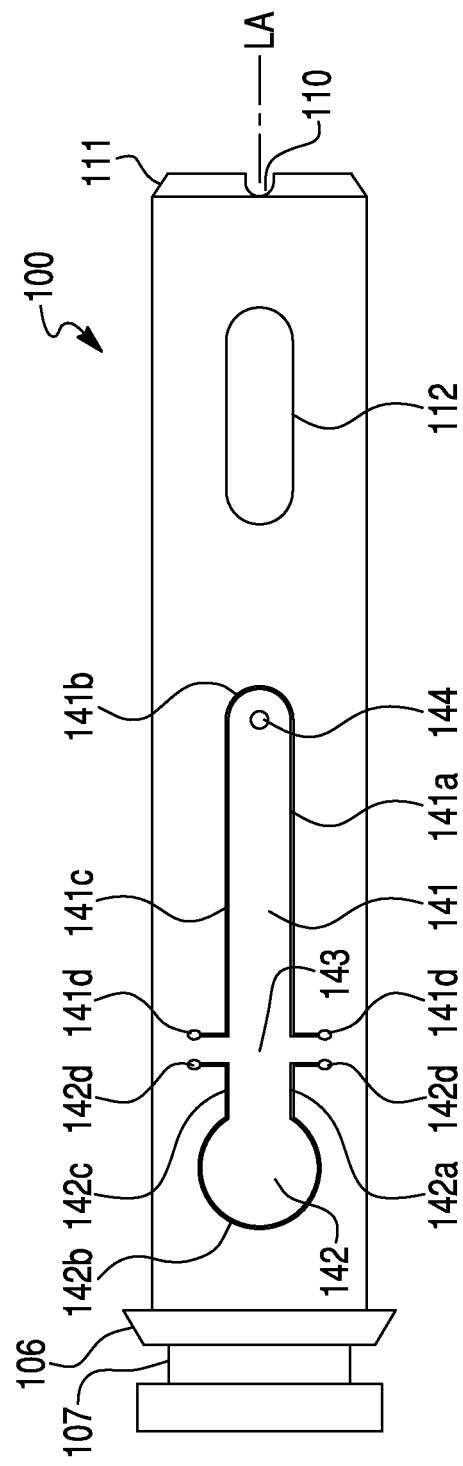
FIG. 5 is a front view of the outer tube of the rod persuader of FIG. 1.

FIG. 5 is a front view of the outer tube 100 of the rod persuader 10. As indicated above, the outer tube 100 can be configured to provide at least three distinct functions: 1) restraining the locking element 300 from expanding to thereby lock the pin 217 of inner tube 200 in engagement with a pedicle screw 800; 2) contacting and pushing the spinal rod 700 when the pedicle screw 800 is locked to the inner tube 200 in order to persuade or push the spinal rod 700 into place in the pedicle screw 800; 3) and selectively providing access to the locking element 300 and inner tube 200 such that disassembly of each of the parts that comprise the rod persuader 10 can occur. The outer tube 100 also includes other structures that permit and guide relative movement of various structures of the rod persuader 10 (e.g., the locking sleeve 300 and inner tube 200).

The outer tube 100 can be cylindrical with a longitudinal axis coincident with the longitudinal axis LA of the rod persuader 10. A proximal end of the outer tube 100 can include a circumferential channel 107 into a which a bearing, such as roller bearing 105, can be located and ultimately connected to a second actuation mechanism 150. An inclined or angled surface 106 can be located adjacent the channel 107 and configured to prevent movement of the second actuation mechanism 150 in the longitudinal axis direction. Furthermore, the proximal end of the outer tube 100 can be configured to rotatably connect to the second actuation mechanism 150 (in conjunction with the bearing located in channel 107).

An example of structural features of the outer tube 100 that permits the function of easy disassembly of the rod persuader 10 will now be described. The outer tube 100 can include a proximal tab 142 and a distal tab 141 connected to each other via a living hinge 143 such that application of force on one of the tabs 141 or 142 causes the other of the tabs to move in a direction opposed to the force direction. For example, placing pressure on tab 142 will cause tab 141 to lift up and away from the cylindrical surface of the outer tube 100. In addition, a pin 144 can be located at a distal end of distal tab 141 and configured to be guided within the outer tube guide slot 213 of the inner tube 200. Thus, when an inward force is applied to tab 142, the tab 141 will move outwardly and the pin 144 will be removed from the guide slot 213. Thus, the outer tube 100 will be free to be disassembled from the inner tube 200 and locking element 300 by rotating the second actuation mechanism 150 to move the outer tube 100 distally until the outer tube 100 is clear of screw threads 210 and can be slid off of the inner tube 200 and locking element 300.

In the depicted embodiment, the tabs 141 and 142 can be formed integrally and from a same and continuous material as a remainder of the outer tube 100. In particular, the proximal tab 142 can be defined by a series of slots formed or machined into the outer tube 100. Specifically, slot 142a can extend substantially linearly and parallel with (i.e., parallel or almost parallel with) the longitudinal axis of the outer tube 100. An aperture 142d can be defined at a distal end of the slot 142a, and a reversing or turning slot 142b can be defined at an opposing proximal end of the slot 142a. A slot 142c can then extend from an opposite end of the reversing or turning slot 142b such that the slots 142a and 142c run substantially parallel with respect to each other and, together with the slot 142b, define the tab 142. Another aperture 142d can be defined at a distal end of the slot 142c.

Likewise, the distal tab 141 can be defined by a series of slots formed or machined into the outer tube 100. Specifically, slot 141a can extend substantially linearly and parallel with (i.e., parallel or almost parallel with) the longitudinal axis of the outer tube 100. An aperture 141d can be defined at a proximal end of the slot 141a, and a reversing or turning slot 141b can be defined at an opposing distal end of the slot 141a. A slot 141c can then extend from an opposite end of the reversing or turning slot 141b such that the slots 141a and 141c run substantially parallel with respect to each other and, together with the slot 141b, define the tab 141. Another aperture 141d can be defined at a distal end of the slot 141c. In addition, the slots 141a-d and slots 142a-d can be aligned to create a living hinge 143 intermediate tabs 141 and 142. In addition, slots 141a and 142a can be substantially co-linear, while slots 141c and 142c can also be substantially co-linear. The alignment and positioning of the slots 141a-d and 142a-d will facilitate the relative motion between the tabs 141 and 142 and the remainder cylindrical portion of the outer sleeve when pressure is applied to, for example, tab 141.

The outer tube 100 can also include a window 112 formed in a distal portion of the cylindrical tube such that certain functions and alignment of structures can be viewed by a user or technician either during or after use of the device. The distal end of the outer tube 100 can be chamfered or beveled in order to easily and safely be inserted adjacent or into a surgical site during use of the rod persuader 10. In addition, the distal end of the tube 100 can include an indent 110 configured to mate with a spinal rod 700. In use, the indent 110 will contact and push the spinal rod 700 (FIG. 10) into position with respect to a head 803 of a pedicle screw 800.

FIGS. 6 and 7 are perspective cross-sectional partial views taken along lines VI-VI and VII-VII of FIG. 2, respectively. These drawings show both the first actuation mechanism 250 and the second actuation mechanism 150 in greater detail. As noted above, the first actuation mechanism 250 can be configured to cause linear movement of the locking element 300 relative to the inner tube 200 to a locked location at which the locking element 300 prevents outward expansion of the distal end of the inner tube 200 to thus maintain engagement of pin(s) 217 to mating structure, such as indents, on the pedicle screws 800. In addition, the second actuation mechanism 150 can be configured to cause the outer tube 100 to push or persuade a spinal rod 700 into position on a pedicle screw 800. Specifically, the second actuation mechanism 150 shown in FIG. 6 includes a set of internal threads 155 that are mated with the external threads 210 of the inner tube 200. A bearing, such as roller bearing 105, can be located between the second actuation mechanism 150 and the outer tube 100 such that the second actuation mechanism 150 can rotate with respect to the outer tube 100. In addition, an angled surface 106 can be provided on the outer tube 100 that mates with a similarly angled surface of the second actuation mechanism 150 so as to prevent motion of the second actuation mechanism 150 with respect to the outer tube 100 in a longitudinal axis direction (facilitates strictly rotational movement between the second actuation mechanism 150 and the outer tube 100). Thus, when the second actuation mechanism 150 is rotated with respect to the outer tube 100, the engagement with the external threads 210 of inner tube 200 ensures that the rotation will translate into linear movement of the second actuation mechanism 150 and outer tube 100 relative to the inner tube 200 in a longitudinal axis direction.

In FIG. 6, the rod persuader 10 is in a locked configuration (i.e., the locking element 300 is fully extended and the distal end of the inner tube 200 is engaged with and locked to the pedicle screw 800). Thus, in this configuration, the outer sleeve 100 can be caused to persuade or push the spinal rod 700 into final position with respect to the engaged pedicle screw 800.

As noted above, the first actuation mechanism 250 can be configured to cause linear movement of the locking element 300 relative to the inner tube 200 to a location at which the locking element 300 prevents outward expansion of the distal end of the inner tube 200 to thus maintain engagement of pin(s) 217 to a mating structure, such as indents, on the pedicle screws 800. The first actuation mechanism 250 is rotatably and slidably connected to the inner tube 200 (albeit in a limited fashion as defined by guiding slot 238). As shown in the cross section of FIG. 6, a pin 258 of the first actuation mechanism 250 is located in a distal and horizontally extending portion 238*b* of the L-shaped slot 238 in the inner tube 200. Thus, in this configuration, the first actuation mechanism 250 and locking element 300 are locked with respect to the position along the longitudinal axis of the inner tube 200.

FIG. 7 shows in better detail the relationship between the first actuation mechanism 250 and the locking element 300. Specifically, the tab 324 of the locking element 300 is shown as located within channel or inner recess 255 of the first actuation mechanism 250. The tab 324 can slide within the recess 255 such that rotation of the first actuation mechanism 250 will not cause the locking element 300 to simultaneously rotate therewith. Moreover, pins 312 and 322 located in the lock plates 310 and 320, respectively, assist in preventing simultaneous rotation of the locking element 300 with the first actuation mechanism 250. In addition, pins 312 and 322 guide the locking element 300 such that the sleeve 300 moves in a linear direction substantially parallel with the longitudinal axis LA of the rod persuader 10 when the first actuation mechanism 250 is also moved in a linear direction substantially parallel with the longitudinal axis LA of the rod persuader 10. The specific location of the cross-section of FIG. 7 shows the locking element 300 extending over the flat portions 220 of the inner tube 200 located between the screw threads 210*a* and 210*b*. Thus, the specific cross-section of FIG. 7 shows the inner threads 155 of the second actuation mechanism 150 unengaged (with the screw threads 210) at this location.

A description of an exemplary method of using the rod persuader 10 and system 1 will now be described with specific reference to FIGS. 8-10. In order to initiate use of the rod persuader 10 and system 1, a user locates the distal end of the inner tube 200 over a spinal rod 700 and then a pedicle screw 800 to which the spinal rod 700 is intended to be affixed. The spinal rod 700 will travel up into the opposed openings 219 located on either side of the distal end of the inner tube 200. Then, the user can use the trumpet-shaped beveled outer distal end of the inner tube 200 to align the inner tube 200 into engagement with the associated pedicle screw 800. The slots 215 located in each of the arms of the distal end of the inner tube 200 will allow the pins 217 and arms to flex outward and ride over the head 803 of the pedicle screw 800 until the pins engage indents in an outer surface of the head 803 of the pedicle screw 800. At this stage, the pedicle screw 800 is considered to be attached to the inner tube 200. In order to lock the pedicle screw 800 to the inner tube 200, the user can, for example, grip the first actuation mechanism 250 with one hand, and the second actuation mechanism 150 with the other hand. The user can then move the first actuation mechanism 250 towards the second actuation mechanism 150. This motion causes the first actuation mechanism 250 to move in a linear fashion parallel with the longitudinal axis LA of the rod persuader 10. The movement can be guided by a pin 258 (attached to the first actuation mechanism 250) sliding or otherwise moving within the first longitudinal portion 238*a* of the L-shaped slot 238 in the inner tube 200 (the first longitudinal portion 238*a* of the L-shaped slot 238 being hidden/covered in FIG. 8 by the locking element 300). Thus, the locking element 300, which is attached to the first actuation mechanism 250, is also moved in a linear longitudinal direction throughout this first motion of the first actuation mechanism 250. The pins 312 and 322 of the lock plates 310 and 320 that make up the locking element 300 slide or otherwise move within longitudinal slots 211 located on either side of the inner tube 200 to guide and ensure linear movement of the locking element 300 with respect to the inner tube 200. Once the pin 258 of the first actuation mechanism 250 reaches the bottom distal most end of the first longitudinal portion 238*a* of the L-shaped slot 238, the pin 258 will contact the wall of the L-shaped slot 238 to prevent further movement in the distal longitudinal direction. At this point, the most distal beveled end of the locking element 300 will be in contact with the distal flexible arms and beveled end of the inner tube 200 to prevent the arms (defined by slots 215) and associated pins 217 from flexing outward and unlocking from the pedicle screw 800 (See FIG. 10). In order to ensure that the locking element 300 does not back out of this locked position, the first actuation mechanism can then be rotated to cause the pin 258 to slide or move within the horizontal portion 238*b* of the L-shaped slot 238 in the inner tube 200 (a portion of slot 238*b* being visible in FIG. 8). The rotation of the first actuation mechanism 250 does not cause the locking element 300 to rotate with respect to the inner tube 200 because pins 312 and 322 are engaged in slots 211 in the inner tube 200, and because the proximal tab 324 of the locking element 300 is rotatably attached within the inner recess 255 of the first actuation mechanism 250. Thus, rotation of the first actuation mechanism 250 causes the pin 258 to be locked in a longitudinal axis direction. In addition, it should be noted that rotation of the first actuation mechanism 250, when at this locked position, is relative to the inner tube 200, outer tube 100, as well as the locking element 300.

Once the pin 258 of the first actuation mechanism 250 is firmly seated at the terminal end of the horizontal portion 238*b* of the L-shaped slot 238 in the inner tube 200, persuasion of the spinal rod 700 into the pedicle screw 800 can begin. Specifically, a user can then begin rotating the second actuation mechanism 150 relative to the inner tube 200, outer tube 100, and the locking element 300. The rotation of the second actuation mechanism 150 causes the internal threads 155 located on an inner circumference of the second actuation mechanism 150 to move along the external threads 210 of the inner tube 200, thus causing the outer tube 100 to move in a linear longitudinal direction with respect to the inner tube 200. Because the inner tube 200 is locked to the pedicle screw 800 and spinal rod 700 via actuation of the first actuation mechanism 250, the linear motion of the outer tube 100 will eventually result in contact between the rod indent 110 in the outer tube 100 and the spinal rod 700. Thereafter, continued rotation of the second actuation mechanism 150 will move the spinal rod 700 downward into the saddle shaped seating in the head 803 of the pedicle screw 800.

Once the spinal rod 700 is adequately seated in the pedicle screw 800, the user can stop rotation of the second actuation mechanism 150 and the outer tube 100 will remain stationary due to friction between the engaged screw threads 155 and 210, and the spinal rod 700 will therefore be held in place within the head 803 of pedicle screw 800. A set screw 510 can then be attached to a distal end of a driver 410 for insertion through a central aperture 10*c* that runs the entire length of the rod persuader 10. The set screw 510 can have external threads 511 that mate with internal threads 804 located on a proximal portion of the U-shaped saddle in the head 803 of pedicle screw 800. The set screw 510 can also include a driving indent 512 that mates with a distal end driving portion 411 of the driver 410. The driver 410 can have a shaft 412 that has a length that is slightly longer then an entire length of the rod persuader 10, and which is attached at a proximal end to a knurled handle 413. The set screw 510 can be attached to the distal end of the driver 410 by frictional engagement between the driving indent 512 of the set screw 510 and the distal end driving portion 411 of the driver, or by other attachment structures or materials, such as adhesives, magnetics, etc. Once the set screw 510 is attached to the driver 410, the set screw 510 can be inserted through the entire length of the central aperture 10c of the rod persuader 10 until the set screw 510 engages the head 803 of the pedicle screw 800. The driver 410 can then be rotated to cause the external threads 511 of the set screw 510 to engage with the internal threads 804 located about an inner periphery of the U-shaped saddle portion of the head 803 of the pedicle screw 800. Once engaged, further rotation of the driver 410 will cause the set screw 510 to move along the inner threads 804 and eventually be driven into contact with the spinal rod 700 to thereby lock the spinal rod 700 firmly in place in the head 803 of the pedicle screw 800. Once the set screw 510 and spinal rod 700 are locked in place, the driver 410 can be removed from the central aperture 10c, and the rod persuader 10 can be disengaged from the pedicle screw 800 and removed from the spinal rod 700.

Disengagement of the rod persuader 10 from the pedicle screw 800 and spinal rod 700 can be accomplished by a reversal of the actuation protocol for the second actuation mechanism 150 and then the first actuation mechanism 250. In particular, once the set screw 510 is in place, the second actuation mechanism 150 can be rotated in a direction opposite to the first rotation direction to cause the outer tube 100 to back away from the spinal rod 700. Once the outer tube 100 is disengaged from the spinal rod 700, the inner tube 200 can be disengaged from the pedicle screw 800. In order to release the inner tube 200 from the pedicle screw 800, the locking element 300 can be moved proximally along the longitudinal axis of the rod persuader 10 to allow the pins 217 and arms defined by slots 215 to flex radially outward away from the longitudinal axis of the rod persuader. The proximal movement of the sleeve 300 can be accomplished by first rotating the first actuation mechanism 250 in a direction such that the pin 258 in the first actuation mechanism 250 moves back along the horizontal portion 238b of the L-shaped slot 238 until the pin 258 reaches the longitudinal direction portion 238a of the slot 238. Once the pin 258 is located at the longitudinal direction portion 238a of the slot 238, the first actuation mechanism 250 can be pulled in a proximal direction by hand to cause both the first actuation mechanism 250 and the locking element 300 to move in a proximal linear motion substantially parallel with the longitudinal axis direction of the rod persuader 10. Then, with the distal end of the locking element 300 out of the way, the arms and the pins 217 of the inner tube 200 are able to flex radially outward away from the longitudinal axis of the rod persuader to disengage from the pedicle screw 800, allowing the entire rod persuader 10 to disengage from the pedicle screw 800 and spinal rod 700.

Once operation of the device is finished, the tabs 141, 142 and living hinge 143 of the outer tube 100 can facilitate quick and easy disassembly of the rod persuader device 10 for cleaning, maintenance, replacement, and/or storage. In particular, a user can pinch or otherwise apply a similar force to either side of the outer tube 100 at a location of the proximal tabs 142 located on opposite sides of the tube 100. The pinching pressure or force on the tabs 141 causes the tabs 142 to lift up and away from the cylindrical surface of the outer tube 100 by action of living hinges 143 that connect the tabs 141 and 142. In addition, a pin 144 can be located at a distal end of each distal tab 141 and can be located within an outer tube guide slot 213 of the inner tube 200 (thus preventing removal of the outer tube 100 from the inner tube 200 when the pin 144 is engaged in the slot 213). Accordingly, when a user pinches the tabs 142, the tabs 141 will move outwardly and the pins 144 will be removed from the guide slots 213. Thus, the outer tube 100 will be free to be disassembled from the inner tube 200 (and locking element 300). Disassembly is accomplished by rotating the second actuation mechanism 150 to move the outer tube 100 distally until it is clear of screw threads 210 and can be slid off of the inner tube 200 and locking element 300 when the pins 144 are disengaged from the slots 213. When the outer tube 100 is removed from the rod persuader 10, the locking element 300 can then be easily removed from the inner tube 200 to fully disassemble the rod persuader 10.

While certain embodiments of the disclosed subject matter are described above, it should be understood that the disclosed subject matter can be embodied and configured in many different ways without departing from the spirit and scope of the invention. For example, the number of various components can be changed without departing from the scope and spirit of the disclosed subject matter. Specifically, pairs of tabs 141, 142, living hinges 143, pins 144, 217, 322, slots 211, 213, 215, and openings 219 are shown. However, a single one of each of these structures could conceivably be used, or a larger plurality of each of these structures could be used. Likewise, while only a single pin 258 is shown for use with the first actuation mechanism 250, it is conceivable that additional pins 258 and additional mating L-shaped grooves 238 in the inner tube 200 could be used with a rod persuader 10 made in accordance with principles of the disclosed subject matter. Furthermore, although the groove 238 is shown as being "L-shaped," many various and different structural shapes are contemplated that could fulfill the function of the slot 238, such as a J-shaped, zig-zag shaped, or even notch shaped slot(s) could be used to carry out the locking function of the first actuation mechanism 250 (and locking element 300) with respect to the inner tube 200.

A reversal of parts for most of the disclosed mating structures is also contemplated to be within the scope of the presently disclosed subject matter. For example, the pins located in the locking element 300, the outer tube 100, the distal end of the inner tube 100, and the first actuation mechanism could all be replaced with slots that mate with pins provided with each corresponding mating structure.

The locking element 300 is shown as including a pair of semi cylindrical plates. However, it should be understood that the structural configuration of the locking element 300 can be varied and different. For example, each lock plate 310, 320 can be configured as a rod like structure that is circular, square, non-symmetrical, or other shape in cross-section.

The first actuation mechanism 250 and second actuation mechanism 150 are shown as generally collar-like cylindrical structures. However, the geometrical shape of each of these structures can be significantly changed without departing from the spirit or scope of the presently disclosed subject matter. For example, the first and/or second actuation mechanisms 250, 150 can be configured as a non-symmetrical handle that extends from the inner tube 200.

The manner in which movement between each of the structures is facilitated can also be changed. For example, the roller bearing 105 that facilitate rotational movement between the second actuation mechanism 150 and the outer tube 100 can be replaced with other known structures or configuration that permit or facilitate such rotational movement, such as, for example, ball bearings, fluid bearings, tapered bearings, frictional surface bearings, and other known bearing structures or configurations.

The tabs 141 and 142 with living hinge 143 can also be replaced with various different structures for facilitating disassembly of the rod persuader 10. In particular, a separate hinge can be used, and tabs 141 and 142 can be configured as separate and distinct structures that are attached and moveable with respect to the outer tube 100. Furthermore, a single tab 141 could be used to facilitate disassembly of the rod persuader 10. It is also contemplated that the pin 144 could simply be screwed into or otherwise removably attached to the outer tube 100 such that removal (or movement) of the pin 144 will facilitate disassembly of the rod persuader 10.

Although the rod persuader 10 is disclosed as having a central through hole extending along the entire length of the rod persuader 10 to facilitate placement and attachment of the set screw 510 onto the head 803 of the pedicle screw 800, the rod persuader 10 could be provided without such a central aperture. For example, a slot can be provided in a side of the rod persuader 10 that would allow insertion of the set screw 510. Alternatively, the pedicle screw 800 could be provided with some structure that temporarily fixes the spinal rod 700 thereto (after persuasion) until a set screw 510 can be secured in place to permanently lock the spinal rod 700 to the pedicle screw 800.

The various structures of the rod persuader 10 can each be assembled from multiple parts and formed of different materials, or can each be constructed as a single homogeneous body of material, rather than an assembly of parts. The material selected for the inner tube 200 can provide for sufficient elasticity at the arms defined by slots 215. In addition, the material can be a biocompatible material. Suitable materials include but are not limited to stainless steel, titanium, other metals, metal alloys, ceramics, plastics, or superelastic shape memory alloys like Nitinol, or combinations thereof. The outer tube 100 and locking element 300 can also be made from a similar material or combination of materials. The actuation mechanisms 150, 250 can be made from a plastic material to reduce the weight of the rod persuader 10, but can just as likely be made from stainless steel, titanium, other metals, metal alloys, ceramics, other plastics, or superelastic shape memory alloys like Nitinol, or combinations thereof. In addition, the spinal rod 700, pedicle screw 800, and set screw 510 can also be made from similar materials or combinations of materials, including stainless steel, titanium, other metals, metal alloys, ceramics, other plastics, or superelastic shape memory alloys like Nitinol, or combinations thereof. The pins 144, 217, 258, 312, and 322 can be made from a hardened metal such that they can be press fit into fitting holes in their respective mating structures. Alternatively, the pins 144, 217, 258, 312, and 322 can be made of a similar material as compared to the structure to which they are attached. The pins 144, 217, 258, 312, and 322 can be adhered to their mating structures by welding, press fit, adhesives or through the use of attachment structure(s) such as a lock pin or set screw.

While the method of use of the rod persuader 10 and system 1 is described in a chronological series of steps, the steps of the method need not be chronological. Instead, certain actions can occur simultaneously or in reverse or different order while remaining within the scope of the presently disclosed subject matter. Additional or different intervening steps can also be included in the method, and/or certain steps and functions can be omitted. For example, a step of bending the spinal rod 700 can be included, while the step of rotating the second actuation mechanism 150 can be excluded if the rod 700 is sufficiently close to the pedicle screw 800 that application of the set screw 510 through central aperture 10c is sufficient to persuade the spinal rod 700 into a final location.

While the subject matter has been described in detail with reference to exemplary embodiments thereof, it will be apparent to one skilled in the art that various changes can be made, and equivalents employed, without departing from the scope of the invention. All related art references discussed in the above Description of the Related Art section are hereby incorporated by reference in their entirety.

What is claimed is:

1. A spinal rod persuader, comprising:
    an outer tube including an outer tube distal end and an outer tube proximal end, the outer tube having a central axis coaxial with and extending along a longitudinal axis of the rod persuader;
    an inner tube including an inner tube distal end and an inner tube proximal end, the inner tube at least partially located in the outer tube;
    a locking element located between the inner tube and the outer tube, the locking element configured to move with respect to the inner tube from a first unlocked position to a second locked position along a longitudinal axis direction of the inner tube;
    a first actuation mechanism connected to the locking element, wherein linear movement of the first actuation mechanism in the longitudinal axis direction causes the locking element to move relative to at least one of the inner tube and outer tube in the longitudinal axis direction; and
    a second actuation mechanism connected to the outer tube, wherein rotation of the second actuation mechanism with respect to the outer tube causes the outer tube to move in the longitudinal axis direction with respect to the inner tube.

2. The spinal rod persuader of claim 1, wherein the outer tube includes a first lock structure located at a first longitudinal axis position of the outer tube and adjacent a guide structure located on the locking element, the first lock structure moveable between a locked position and an unlocked position, wherein when the first lock structure is located in the unlocked position, the guide structure of the locking element is permitted to move such that the locking element can be disassembled from the outer tube and the inner tube, and when the first lock structure is located in the locked position, the locking element is prevented from being disassembled from the outer tube and the inner tube.

3. The spinal rod persuader of claim 2, wherein the first lock structure includes a first slot having a first slot first portion extending parallel relative to the central axis of the outer tube, a first slot second portion extending parallel to the first slot first portion, and a first slot intermediate portion connected to ends of the first and second portions of the first slot, wherein the first, second and intermediate portions of the first slot define a moveable tab.

4. The spinal rod persuader of claim 3, wherein
    the first lock structure further includes a second slot having a second slot first portion extending parallel relative to the central axis of the outer tube, a second slot second portion extending parallel to the second slot first portion, and a second slot intermediate portion connected to ends of the first and second portions of the second slot.

5. The spinal rod persuader of claim 1, wherein
    the second actuation device includes a cylinder rotatably connected with respect to the outer tube and having an internal thread, and wherein the inner tube includes an external thread that mates with an internal thread of the second actuation device.

6. The spinal rod persuader of claim 1, wherein the locking element includes a guide structure configured to guide movement of the locking element with respect to at least one of the outer tube and the inner tube, wherein the guide structure includes a pin extending substantially perpendicular to the longitudinal axis of the rod persuader, and the inner tube includes a slot in which the pin is guided during movement.

7. The spinal rod persuader of claim 1, wherein the inner tube includes a slot defined therein; and the first actuation mechanism includes a collar located at a proximal end of the locking element, the collar includes a pin extending substantially perpendicular to the longitudinal axis of the rod persuader and within the slot in the inner tube, wherein the slot has a longitudinal portion and a lock portion configured such that the first actuation mechanism is locked in a longitudinal axis position with respect to the inner tube when the pin is located within the lock portion of the slot, and the first actuation mechanism is permitted to move along the longitudinal axis when the pin is located in the longitudinal portion of the slot.

8. The spinal rod persuader of claim 1, wherein the locking element is configured such that when the locking element is located in the second locked position, the inner tube is prevented from moving in at least one direction by the locking element, and when the locking element is located in the first unlocked position, the inner tube is permitted to move in the at least one direction.

9. The spinal rod persuader of claim 1, wherein the locking element is rotatably connected to the first actuation mechanism.

10. The spinal rod persuader of claim 9, wherein the inner tube includes a slot defined therein; and the first actuation mechanism includes a collar located at a proximal end of the locking element, the collar includes a pin extending substantially perpendicular to the longitudinal axis of the rod persuader and within the slot in the inner tube, wherein the slot has a longitudinal portion and a lock portion configured such that the first actuation mechanism is locked in a longitudinal axis position with respect to the inner tube when the pin is located within the lock portion of the slot, and the first actuation mechanism is permitted to move along the longitudinal axis when the pin is located in the longitudinal portion of the slot.

11. The spinal rod persuader of claim 1, wherein the inner tube includes screw threads located at the proximal end of the inner tube, and the screw threads include a first set of screw threads and a second set of screw threads separated from the first set of screw threads by a first non-threaded space and a second non-threaded space, each of first non-threaded space and second non-threaded space extends parallel with the longitudinal axis of the rod persuader such that the first set of screw threads are formed in a semi-circle and the second set of screw threads are formed in a second semi-circle; the locking element includes a first plate and a second plate, the first plate located between the first set of screw threads and second set of screw threads and along the first non-threaded space of the inner tube, and the second plate located between the first set of screw threads and second set of screw threads and along the second non-threaded space of the inner tube such that a longitudinal axis of the first plate and a longitudinal axis of the second plate are substantially parallel with respect to each other.

12. The spinal rod persuader of claim 1, wherein the locking element comprises first and second lock plates disposed on opposite sides of the inner tube with a gap defined between each longitudinally extending and opposing free end of the first and second lock plates, wherein the first and second lock plates are disposed intermediate the inner tube and the outer tube in a direction extending radially away from a longitudinal axis of the rod persuader.

13. The spinal rod persuader of claim 1, wherein the outer tube includes an indent located at the outer most portion of the distal end of the outer tube such that the outer tube is configured to engage a spinal rod and persuade the spinal rod into position by movement of the outer tube relative to the inner tube when the indent engages the spinal rod.

14. A spinal rod system, comprising:
the spinal rod persuader as defined in claim 1;
a pedicle screw including a threaded portion and a saddle shaped head portion configured to be engaged by the inner tube of the spinal rod persuader; and
a spinal rod configured to be located within the saddle shaped head portion of the pedicle screw.

15. The spinal rod system of claim 14, further comprising:
a set screw configured to be insertable into and along a central aperture in the spinal rod persuader.

16. The spinal rod system of claim 15, wherein the central aperture of the spinal rod persuader has a central axis coaxial with the longitudinal axis of the spinal rod persuader, and the central aperture extends along an entire length of the spinal rod persuader such that the set screw is insertable into the central aperture at the proximal end of the outer tube and such that the set screw is attachable to the head of the pedicle screw while the inner tube is connected to the head of the pedicle screw.

17. The spinal rod system of claim 14, further comprising:
a driver configured to insert the set screw into the central aperture of the spinal rod persuader and to attach the set screw to the head of the pedicle screw.

18. A method of making a spinal rod persuader, comprising:
providing an outer tube including an outer tube distal end and an outer tube proximal end, the outer tube defining a longitudinal axis of the road persuader, an inner tube including an inner tube distal end and an inner tube proximal end, the inner tube at least partially located in the outer tube, a locking element located between the inner tube and the outer tube, a first actuation mechanism located at a first position along the longitudinal axis of the rod persuader, and a second actuation mechanism located at a second position along the longitudinal axis of the rod persuader;
moving the first actuation mechanism in a linear motion along the longitudinal axis of the rod persuader to cause the locking element to move along the longitudinal axis of the rod persuader; and
rotating the second actuation mechanism relative to the outer tube to cause the outer tube to move along the longitudinal axis of the rod persuader.

19. The method of making a spinal rod persuader of claim 18, further comprising:
rotating the first actuation mechanism about the longitudinal axis of the rod persuader to cause the locking element to be locked at a longitudinal axis position with respect to the inner tube.

20. The method of making a spinal rod persuader of claim 18, wherein
rotating the second actuation mechanism relative to the outer tube causes the outer tube to press against a spinal rod to insert the spinal rod into a head portion of a pedicle screw.

21. The method of making a spinal rod persuader of claim 18, wherein
moving the first actuation mechanism in a linear motion along the longitudinal axis of the rod persuader causes the locking element to prevent the inner tube from moving in an outward direction away from the longitudinal axis of the persuader.

22. A spinal rod persuader, comprising:
an outer tube including an outer tube distal end and an outer tube proximal end;
an inner tube including an inner tube distal end and an inner tube proximal end, the inner tube at least partially located in the outer tube;
a locking element located between the inner tube and the outer tube, the locking element including a guide structure configured to guide movement of the locking element with respect to at least one of the outer tube and the inner tube, the locking element further including first and second lock plates disposed on opposite sides of the inner tube with a gap defined between each longitudinally extending and opposing free end of the first and second lock plates, wherein the first and second lock plates are disposed intermediate the inner tube and the outer tube in a direction extending radially away from a longitudinal axis of the rod persuader, wherein
the outer tube includes a first lock structure located at a first longitudinal axis position of the outer tube and adjacent the guide structure of the locking element, the first lock structure moveable between a locked position and an unlocked position, wherein when the first lock structure is located in the unlocked position, the guide structure of the locking element is permitted to be disassembled from the outer tube and the inner tube, and when the first lock structure is located in the locked position, the guide structure of the locking element is not permitted to be disassembled from the outer tube and the inner tube.

23. The spinal rod persuader of claim 22, wherein
the first lock structure includes a first slot having a first portion running along a longitudinal axis of the outer tube, a turn portion located at an end of the first portion, and a second portion running along the longitudinal axis of the outer tube.

24. The spinal rod persuader of claim 23, wherein
the first lock structure includes a second slot having a second slot first portion running along a longitudinal axis of the outer tube, a second slot turn portion located at an end of the second slot first portion, and a second slot second portion running back along the longitudinal axis of the outer tube.

25. The spinal rod persuader of claim 24, wherein
the first slot first portion and the second slot first portion include at least portions that are co-linear with each other, and the first slot second portion and the second slot second portion include at least portions that are co-linear with each other, such that the first slot defines a first tab and the second slot defines a second tab.

26. The spinal rod persuader of claim 24, wherein
the first slot defines a first tab and the second slot defines a second tab, and the first tab is configured such that when a force is applied to the first tab in a direction towards a central longitudinal axis of the outer tube, the first tab moves towards the central longitudinal axis of the outer tube while the second tab simultaneously moves away from the central longitudinal axis of the outer tube.

27. The spinal rod persuader of claim 22, wherein
the guide structure of the locking element includes a pin configured to ride within a slot located in at least one of the outer tube and the inner tube.

28. The spinal rod persuader of claim 22, wherein
the inner tube includes a set of screw threads located at the proximal end of the inner tube, the screw threads including opposing flats that separate a first set of the screw threads from a second set of the screw threads, wherein the first lock plate is located in a first of the opposing flats, and the second lock plate is located in a second of the opposing flats.

29. The spinal rod persuader of claim 22, wherein the first lock structure includes a first tab portion integral with and comprising a same and continuous material with a remaining cylindrical portion of the outer tube, the first tab portion being moveable between the locked position and the unlocked position with respect to the remaining cylindrical portion of the outer tube.

30. The spinal rod persuader of claim 22, further comprising:
a first actuation mechanism connected to the locking element such that linear movement of the first actuation mechanism in a direction parallel with the longitudinal axis causes the locking element to move relative to at least one of the inner tube and outer tube in the direction parallel with the longitudinal axis; and
a second actuation mechanism connected to the outer tube such that rotation of the second actuation mechanism with respect to the outer tube causes the outer tube to move in the direction parallel with the longitudinal axis and with respect to the inner tube.

* * * * *